US008545872B2

(12) United States Patent
Breitenbach

(10) Patent No.: US 8,545,872 B2
(45) Date of Patent: Oct. 1, 2013

(54) DEVICE FOR THE TRANSDERMAL ADMINISTRATION OF A ROTIGOTINE BASE

(75) Inventor: Armin Breitenbach, Monheim (DE)

(73) Assignee: UCB Pharma GmbH, Monheim (DE)

( * ) Notice: Subject to any disclaimer, the term of this patent is extended or adjusted under 35 U.S.C. 154(b) by 0 days.

(21) Appl. No.: 13/020,414

(22) Filed: Feb. 3, 2011

(65) Prior Publication Data
US 2011/0165247 A1    Jul. 7, 2011

Related U.S. Application Data

(63) Continuation of application No. 10/517,157, filed as application No. PCT/EP03/14902 on Dec. 24, 2003, now abandoned.

(30) Foreign Application Priority Data

Dec. 30, 2002    (DE) .................................. 102 61 696

(51) Int. Cl.
*A61K 31/381*    (2006.01)
*A61K 9/70*    (2006.01)

(52) U.S. Cl.
USPC ............ 424/449; 424/486; 424/484; 514/438

(58) Field of Classification Search
None
See application file for complete search history.

(56) References Cited

U.S. PATENT DOCUMENTS

| | | | |
|---|---|---|---|
| 4,863,970 A | 9/1989 | Patel et al. ..................... | 514/772 |
| 4,915,950 A | 4/1990 | Miranda et al. ................ | 424/448 |
| 4,973,468 A | 11/1990 | Chiang et al. ................. | 424/449 |
| 5,043,482 A | 8/1991 | Maignan et al. ............... | 568/734 |
| 5,069,909 A | 12/1991 | Sharma et al. ................. | 424/449 |
| 5,091,186 A | 2/1992 | Miranda et al. ................ | 424/448 |
| 5,124,157 A | 6/1992 | Colley et al. ................... | 424/448 |
| 5,147,916 A | 9/1992 | Sweet ............................ | 524/266 |
| 5,177,112 A | 1/1993 | Horn ............................... | 514/65 |
| 5,225,198 A | 7/1993 | Sharma et al. ................. | 424/443 |
| 5,234,690 A | 8/1993 | Chiang et al. ................. | 424/448 |

(Continued)

FOREIGN PATENT DOCUMENTS

| | | |
|---|---|---|
| CA | 2 532 804 | 2/2005 |
| CA | 2 532 859 | 2/2005 |

(Continued)

OTHER PUBLICATIONS

Blindauer (2003) Arch. Neurol. 60(12): 1721-1728.

(Continued)

*Primary Examiner* — Rachael E Bredefeld
(74) *Attorney, Agent, or Firm* — Harness, Dickey & Pierce, P.L.C.

(57) ABSTRACT

The invention relates to a polymer matrix suitable for the transdermal administration of rotigotine [(−)-5, 6, 7, 8-tetrahydro-6-[propyl[2-(2-thienyl)ethyl]amino]-1-naphtol], containing a matrix for the transdermal administration of rotigotine [(−)-5, 6, 7, 8-tetrahydro-6-[propyl[2-(2-thienyl)ethyl]amino]-1 naphtol], containing a matrix polymer which is supersaturated with a rotigotine base. Said polymer matrix is characterised in that the part of the rotigotine which is not dissolved in the matrix polymer is dispersed in the matrix polymer as amorphous particles having a maximum mean diameter of 30 μm, and the matrix is free of solubilisers, crystallisation inhibitors and dispersants. The invention also relates to a flat device for the transdermal administration of rotigotine, containing the above-mentioned, preferably silicon-based polymer matrix which is supersaturated with rotigotine, and a rear layer which is impermeable to the active ingredient.

11 Claims, 6 Drawing Sheets

Matrix according to the invention with amorphous rotigotine particles

(56) References Cited

U.S. PATENT DOCUMENTS

| | | | |
|---|---|---|---|
| 5,246,997 A | 9/1993 | Sweet | 524/266 |
| 5,252,334 A | 10/1993 | Chiang et al. | 424/448 |
| 5,252,335 A | 10/1993 | Chiang | 424/449 |
| 5,271,940 A | 12/1993 | Cleary et al. | 424/448 |
| 5,273,755 A | 12/1993 | Venktraman et al. | 424/448 |
| 5,273,756 A | 12/1993 | Fallon et al. | 424/448 |
| 5,273,757 A | 12/1993 | Jaeger et al. | 424/448 |
| 5,308,625 A | 5/1994 | Wong et al. | 424/449 |
| 5,382,596 A | 1/1995 | Sleevi et al. | 514/459 |
| 5,393,529 A | 2/1995 | Hoffman et al. | 424/445 |
| 5,456,745 A | 10/1995 | Roreger et al. | 106/128 |
| 5,554,381 A | 9/1996 | Roos et al. | 424/449 |
| 5,601,839 A | 2/1997 | Quan et al. | 424/448 |
| RE35,474 E | 3/1997 | Woodard et al. | 424/448 |
| 5,658,975 A | 8/1997 | Ulman et al. | 524/266 |
| 5,670,164 A | 9/1997 | Meconi et al. | 424/448 |
| 5,688,524 A | 11/1997 | Hsu et al. | 424/449 |
| 5,733,571 A | 3/1998 | Sackler | 424/449 |
| 5,771,890 A | 6/1998 | Tamada | 128/635 |
| 5,807,570 A | 9/1998 | Chen et al. | 424/449 |
| 5,834,010 A | 11/1998 | Quan et al. | 424/448 |
| 5,840,336 A | 11/1998 | Hsu et al. | 424/484 |
| 5,843,472 A | 12/1998 | Ma et al. | 424/449 |
| 5,876,746 A | 3/1999 | Jona et al. | 424/449 |
| 5,879,701 A | 3/1999 | Audett et al. | 424/448 |
| 5,891,461 A | 4/1999 | Jona et al. | 424/449 |
| 5,902,603 A | 5/1999 | Chen et al. | 424/449 |
| 5,906,830 A | 5/1999 | Farinas et al. | 424/448 |
| 5,980,932 A | 11/1999 | Chiang et al. | 424/448 |
| 6,024,974 A | 2/2000 | Li | 424/448 |
| 6,024,976 A | 2/2000 | Miranda et al. | 424/449 |
| 6,063,398 A | 5/2000 | Gueret | 424/443 |
| 6,218,421 B1 | 4/2001 | King | 514/421 |
| 6,316,022 B1 | 11/2001 | Mantelle et al. | 424/448 |
| 6,372,920 B1 | 4/2002 | Minaskanian et al. | 549/75 |
| 6,393,318 B1 | 5/2002 | Conn et al. | 604/20 |
| 6,398,562 B1 | 6/2002 | Butler et al. | 439/91 |
| 6,465,004 B1 | 10/2002 | Rossi-Montero et al. | 424/448 |
| 6,620,429 B1 | 9/2003 | Müller | 424/449 |
| 6,685,959 B1 | 2/2004 | Moreau et al. | 424/449 |
| 6,699,498 B1 | 3/2004 | Müller | 424/449 |
| 6,884,434 B1 | 4/2005 | Muller et al. | 424/487 |
| 6,899,894 B1 | 5/2005 | Klein et al. | 424/448 |
| 7,309,497 B2 | 12/2007 | Rimpler et al. | 424/422 |
| 7,413,747 B2 | 8/2008 | Mueller et al. | 424/448 |
| 2002/0110585 A1 | 8/2002 | Godbey et al. | 424/449 |
| 2003/0026830 A1 | 2/2003 | Lautertback et al. | 424/449 |
| 2003/0027793 A1 | 2/2003 | Lautertback et al. | 514/63 |
| 2003/0166709 A1 | 9/2003 | Rimpler et al. | 514/447 |
| 2004/0034083 A1 | 2/2004 | Stephenson et al. | 514/406 |
| 2004/0048779 A1 | 3/2004 | Schollmayer | 514/2 |
| 2004/0057985 A1 | 3/2004 | Bracht | 424/449 |
| 2004/0081683 A1 | 4/2004 | Schacht et al. | 424/449 |
| 2004/0110673 A1 | 6/2004 | Steinkasserer et al. | 514/12 |
| 2004/0116537 A1 | 6/2004 | Li et al. | 514/663 |
| 2004/0137045 A1 | 7/2004 | Breitenbach et al. | 424/449 |
| 2004/0209861 A1 | 10/2004 | Benavides et al. | 514/210.01 |
| 2005/0033065 A1 | 2/2005 | Mueller et al. | 549/74 |
| 2005/0079206 A1 | 4/2005 | Schacht et al. | 424/449 |
| 2005/0136101 A1 | 6/2005 | Berthold | 424/449 |
| 2005/0175678 A1 | 8/2005 | Breitenbach | 424/448 |
| 2005/0197385 A1 | 9/2005 | Scheller et al. | 514/438 |
| 2005/0260254 A1 | 11/2005 | Breitenbach et al. | 424/449 |
| 2006/0222691 A1 | 10/2006 | Cantor et al. | 424/448 |
| 2006/0263419 A1 | 11/2006 | Wolff | 424/448 |
| 2007/0072917 A1 | 3/2007 | Scheller et al. | 514/357 |
| 2007/0093546 A1 | 4/2007 | Scheller et al. | 514/447 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller | 514/357 |
| 2008/0274061 A1 | 11/2008 | Schollmayer et al. | 424/45 |
| 2009/0143460 A1 | 6/2009 | Wolff et al. | 514/438 |
| 2010/0311806 A1 | 12/2010 | Wolff et al. | 514/438 |

FOREIGN PATENT DOCUMENTS

| | | |
|---|---|---|
| CA | 2 547 820 | 6/2005 |
| CA | 2 546 797 | 7/2005 |
| EP | 0 180 377 | 5/1986 |
| EP | 1256340 | 11/2002 |
| WO | WO 92/14442 | 3/1992 |
| WO | WO 93/07842 | 4/1993 |
| WO | WO 93/14727 | 8/1993 |
| WO | WO 93/16073 | 8/1993 |
| WO | WO 94/04109 | 3/1994 |
| WO | WO 94/07468 | 4/1994 |
| WO | WO 95/00122 | 1/1995 |
| WO | WO 95/01767 | 1/1995 |
| WO | WO 95/05137 | 2/1995 |
| WO | WO 95/05138 | 2/1995 |
| WO | WO 95/24776 | 9/1995 |
| WO | WO 96/39136 | 12/1995 |
| WO | WO 96/40087 | 12/1995 |
| WO | WO 96/00110 | 1/1996 |
| WO | WO 96/22083 | 7/1996 |
| WO | WO 96/22084 | 7/1996 |
| WO | WO 97/09971 | 3/1997 |
| WO | WO 97/11696 | 4/1997 |
| WO | WO 97/29735 | 8/1997 |
| WO | WO 99/49852 | 10/1999 |
| WO | WO 02/089777 | 11/2002 |
| WO | WO 02/089778 | 11/2002 |

OTHER PUBLICATIONS

Chiang, et al. (1995) Proc. Int. Symp. Controlled Release Bioact. Mater. 22, 710-711.
den Daas, et al. (1990) Naunyn-Schmiedegerg's Pharmacol. 342: 655-659.
Hsu, et al. (1992) Cygnus Therapeutic Systems Project Report N-0923, 2-19.
International Search Report for PCT/EP2003/014902 dated Jul. 15, 2004.
Levien, et al. (2005) Advances in Pharmacy 3(1): 62-92.
LeWitt, et al. (2005) Adjunctive Treatment of Advanced Parkinson's Disease with Rotigotine Transdermal System (PREFER Study), manuscript (25 pp).
Loschman, et al. (1989) Eur. J. Pharmacol. 373-380.
Pfister (1988) Drug and Cosmetic Ind. (Oct): 44-52.
Pfister (1989) Pharm. Tech. (March): 126-138.
Pfister and Hsieh (1990) Pharm. Tech. (Sept): 132-140.
Pfister and Hsieh (1990) Pharm. Tech. (Oct): 54-60.
Pfister, et al. (1991) Chemistry in Britain (Jan): 43-46.
Pfister, et al. (1992) Pharm. Tech. (Jan): 42-58 and 83.
Roy, et al. (1996) J. Pharm. Science 85(5): 491-495.
Swart, et al. (1992) Internatl. J. of Pharmaceutics 88: 165-170.
Tanojo, et al. (1997) "New design of a flow-through permeation cell for studying in vitro permeation studies across biological membranes" Journal of Controlled Release, 45:41-47.
Thomas, et al. (1991) STP Pharma Sci 1(1): 38-46.
Van der Weide, et al. (1988) "The enantiomers of the D-2 dopamine receptor agonist N-0437 discriminate between pre- and postsynaptic dopamine receptors." Eur J Pharmacol 146:319-326.
http://www.ema.europa.eu/humandocs/PDFs/EPAR/neupro/062606en6.pdfm (2006).
Office Action, dated Aug. 17, 2007 issued in U.S. Appl. No. 10/623,864.
Office Action, dated Jan. 6, 2010 issued in U.S. Appl. No. 10/623,864.
Office Action, dated Jun. 24, 2009 issued in U.S. Appl. No. 10/623,864.
Office Action, dated Nov. 12, 2008 issued in U.S. Appl. No. 10/623,864.
Office Action, dated Aug. 31, 2010 issued in U.S. Appl. No. 10/623,864.

Office Action, dated May 12, 2011 issued in U.S. Appl. No. 10/623,864.
Office Action, dated Aug. 18, 2009 issued in U.S. Appl. No. 10/627,990.
Office Action, dated Feb. 2, 2009 issued in U.S. Appl. No. 10/627,990.
Office Action, dated Jan. 4, 2011 issued in U.S. Appl. No. 10/627,990.
Office Action, dated Dec. 23, 2009 issued in U.S. Appl. No. 10/429,283.
Office Action, dated Jan. 8, 2008 issued in U.S. Appl. No. 10/429,283.
Office Action, dated Mar. 30, 2009 issued in U.S. Appl. No. 10/429,283.
Office Action, dated Sep. 12, 2008 issued in U.S. Appl. No. 10/429,283.
Office Action, dated Sep. 21, 2006 issued in U.S. Appl. No. 10/429,283.
Office Action, dated Oct. 1, 2010 issued in U.S. Appl. No. 10/429,283.
Office Action, dated May 4, 2011 issued in U.S. Appl. No. 10/429,283.
Office Action, dated Feb. 19, 2009 issued in U.S. Appl. No. 10/713,424.
Office Action, dated Jun. 25, 2008 issued in U.S. Appl. No. 10/713,424.
Office Action, dated Mar. 23, 2007 issued in U.S. Appl. No. 10/713,424.
Office Action, dated Sep. 14, 2007 issued in U.S. Appl. No. 10/713,424.
Office Action, dated May 1, 2008 issued in U.S. Appl. No. 10/936,620.
Office Action, dated Sep. 13, 2007 issued in U.S. Appl. No. 10/936,620.
Office Action, dated Jan. 23, 2008 issued in U.S. Appl. No. 11/931,666.
Office Action, dated Jun. 9, 2010 issued in U.S. Appl. No. 11/931,762.
Office Action, dated Oct. 15, 2009 issued in U.S. Appl. No. 10/139,894.
Office Action, dated Apr. 27, 2010 issued in U.S. Appl. No. 10/627,990.
Office Action, dated Nov. 24, 2009 issued in U.S. Appl. No. 10/517,157.
Office Action, dated Aug. 6, 2008 issued in U.S. Appl. No. 10/517,157.
Office Action, dated Mar. 6, 2009 issued in U.S. Appl. No. 10/517,157.
Office Action, dated Aug. 3, 2010 issued in U.S. Appl. No. 10/517,157.
Office Action, dated May 12, 2011 issued in U.S. Appl. No. 11/239,701.
Office Action, dated Apr. 19, 2011 issued in U.S. Appl. No. 10/565,713.

Matrix with rotigotine particles after dispersion without solubilizers and/or emulsifier Matrix according to the invention with amorphous rotigotine particles Example of a schematic structure of a monolithic TTS

DEVICE FOR THE TRANSDERMAL ADMINISTRATION OF A ROTIGOTINE BASE

CROSS-REFERENCE TO RELATED APPLICATIONS

This application is a continuation of co-pending application Ser. No. 10/517,157 which is a national stage entry under 35 U.S.C. §371 of International Application No. PCT/EP03/014902 filed on 24 Dec. 2003, which claims the benefit of German Application No. 102 61 696.5 filed on 30 Dec. 2002. Each of the above referenced applications is incorporated herein by reference in its entirety.

BACKGROUND OF THE INVENTION

The present invention relates to a matrix suitable for transdermal administering of rotigotine [(−)-5,6,7,8-tetrahydro-6-[propyl[2-(2-thienyl)ethyl]amino]-1-naphtol] that is free of solubilizers and dispersants and that comprises at least one matrix polymer and rotigotine base in a concentration above the solubility limit of the matrix polymer for rotigotine, wherein the portion of the rotigotine not dissolved in the matrix polymer is dispersed in the matrix polymer as amorphous particles with a maximum mean diameter of 30 μm.

Furthermore, the invention relates to a planiform system for transdermal administering of rotigotine, that contains the above-described preferably silicon-based matrix supersaturated with rotigotine and a backing impermeable for the active substance.

Various silicon-based transdermal systems for administering rotigotine are known from the state of the art.

WO 94-07468 discloses a transdermal system that contains an active substance salt in a two-phase matrix. The two-phase matrix consists of a hydrophobic matrix polymer with a silicate dispersed therein to absorb the hydrophilic pharmaceutical substance salt, wherein hydrophobic solvents are additionally used. The matrix is produced by drying the dispersion at 70° C. The rotigotine content in the matrix is 2-5 weight percent.

This system has several disadvantages, however:

The production is in several stages and expensive. The active substance must be dissolved, then mixed with the silicate, then mixed with an emulsifier, in order to finally emulsify e.g. in a silicon contact adhesive, the solution with the matrix polymer dissolved in an organic solvent—typically heptane, ethyl acetate or toluol.

The resulting emulsion is difficult to handle.

The active substance charge is limited by the solubility of the rotigotine in the respective solvent system. In addition, when removing the solvent during production a concentration takes place, during which an undesirable crystal formation may occur. The maximum quantity of active substance that can be worked into the matrix is limited by this as well. On the other hand, a low active substance charge limits the release capacity of the matrix per unit of time and/or its useful life.

The silicate or silicon dioxide remaining in the plaster represents a diffusion barrier for the active substance, which can negatively affect the release of the active substance.

The anorganic silicate influences the water absorption of the plaster. Pore formation by the dissolving away of water soluble matrix components at the boundary surface adjacent to the skin can lead to a poorly controllable release of the active substance.

WO 99/49852 describes a Transdermal Therapeutic System (TTS) containing a contact adhesive system based on acrylate or silicon, in which rotigotine is present in free-base form. The disclosed TTS allows therapeutically relevant flow rates of rotigotine through human skin.

Rotigotine is only feebly soluble in hydrophobic polymers such as silicon, for example. For these reasons, in WO 99/49852 the adding of additives to improve the solution characteristics of the rotigotine is recommended. This is a matter of in particular hydrophilic polymers such as polyvinyl pyrrolidone (PVP), copolymers of vinyl pyrrolidone and vinyl acetate, polyethylene glycol polypropylene glycol, copolymers of ethylene and vinyl acetate as well as glycerin and its ester.

WO 02/089778 and WO 02/089777 also describe a solvent-based transdermal system for administering rotigotine. According to WO 02/089778 and WO 02/089777, surface-active substances or amphiphilic substances are also added as crystallization inhibitor.

It was thus the technical problem of the present invention to provide a matrix that is simply structured and contains as few accessory substances as possible, but still allows the administering of rotigotine through the skin in therapeutically relevant flow rates, is stable for storage and allows rotigotine base to be worked in a wide range of concentration levels.

DESCRIPTION OF THE INVENTION

Rotigotine base is present as a solid in the form of crystals that are nearly insoluble in the solvents suitable for dissolving matrix polymers, e.g. hexane, ethyl acetate and toluol.

Figure 1:
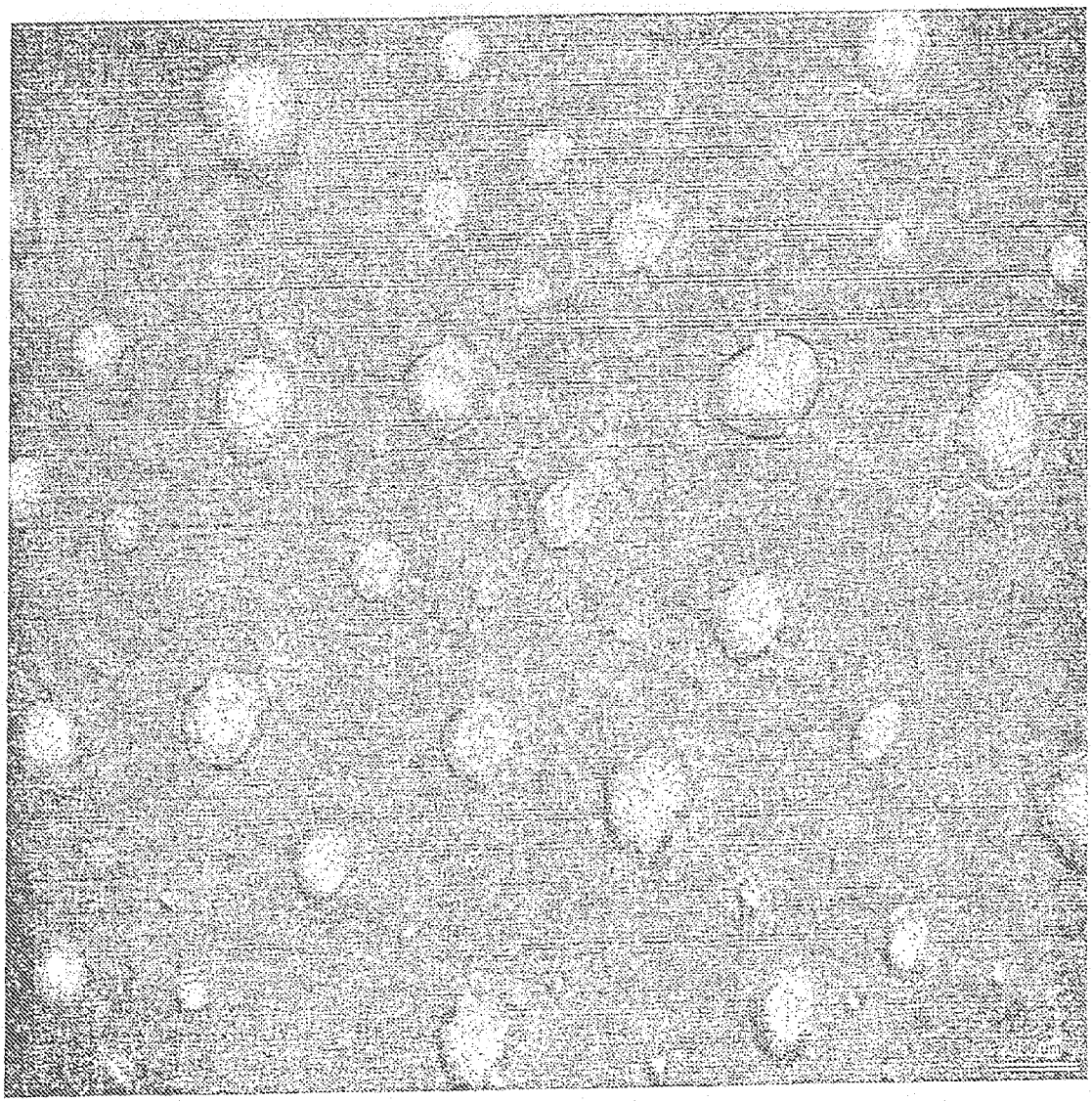
FIG. 1 shows a microscope photo of amorphous rotigotine particles in a silicon matrix that was produced according to example of execution 2b (comparison example) in the solvent method without dispersants

To produce a rotigotine-containing matrix, according to the state of the art the rotigotine crystals are therefore first dissolved in solvents, e.g. ethanol and then added to the polymer phase, e.g. in hexane. To produce a fine dispersion of the active substance-containing phase in the polymer phase, dispersans are used such as the hydrophilic polymers mentioned in WO 99/49852. If the dispersants are not added in this method as recommended, large islands of active substance may form (FIG. 1). These then conceal the risk of skin irritation, recrystallization of the active substance, reduced adhesion of the adhesive matrix and fluctuation of the active substance charge.

It was then surprisingly ascertained that the use of an additional solvent or dispergent and/or crystallization inhibitor can still be dispensed with, if one dispenses with the preliminary dissolving of the rotigotine in solvent, e.g. in ethanol, before introduction into a matrix, e.g. a silicon matrix.

In a form of execution of the invention, the rotigotine base is, for example stirred in crystalline form into a solution of a silicon polymer, e.g. an amino-resistant silicon contact adhesive, in heptane, toluol or ethyl acetate, the mixture is coated onto a foil, e.g. a siliconized polyester foil, and the solvent is removed by drying at 50° C. Then the matrix is heated ("tempered") to a temperature above the melting point of rotigotine, i.e., above approx. 74° C. until the rotigotine crystals have melted. Finally, the matrix is cooled to room temperature. The rotigotine is then present in the form of amorphous particles or drops finely distributed in the silicon-based matrix.

Figure 2:
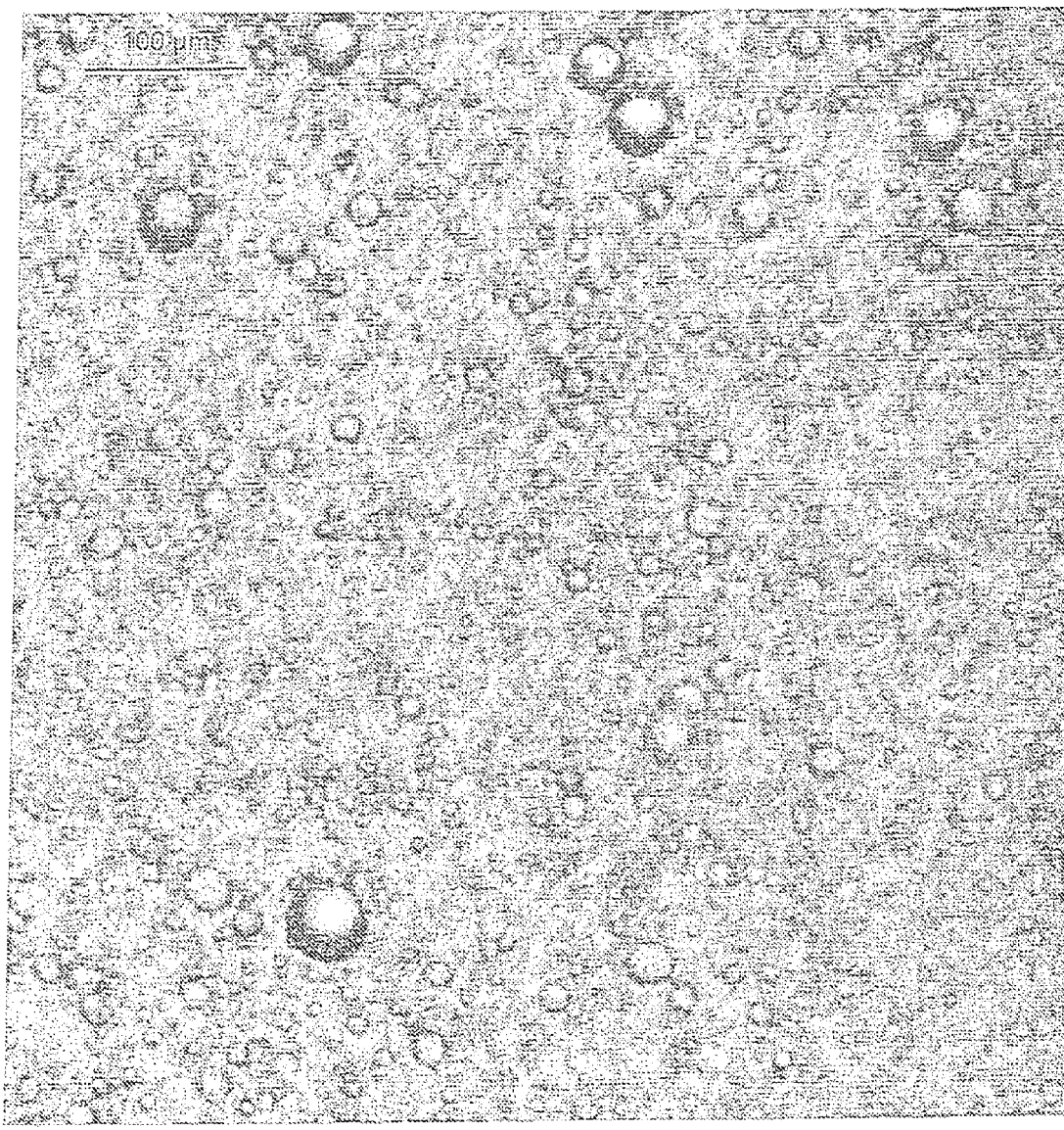
FIG. 2 shows microscopic photos of amorphous rotigotine particles in a silicon matrix according to the invention that was produced according to example of execution 1 by "tempering" without dispersants.

Upon observation through the microscope, it turned out that the amorphous rotigotine particles are surprisingly finely distributed in the silicon matrix, with a maximum size of roughly 30-40 μm, but mostly smaller than 20 μm (FIG. 2). Even after six months storage at room temperature, the amorphous rotigotine particles in the silicon matrix showed no tendency to recrystallize.

Figure 3:
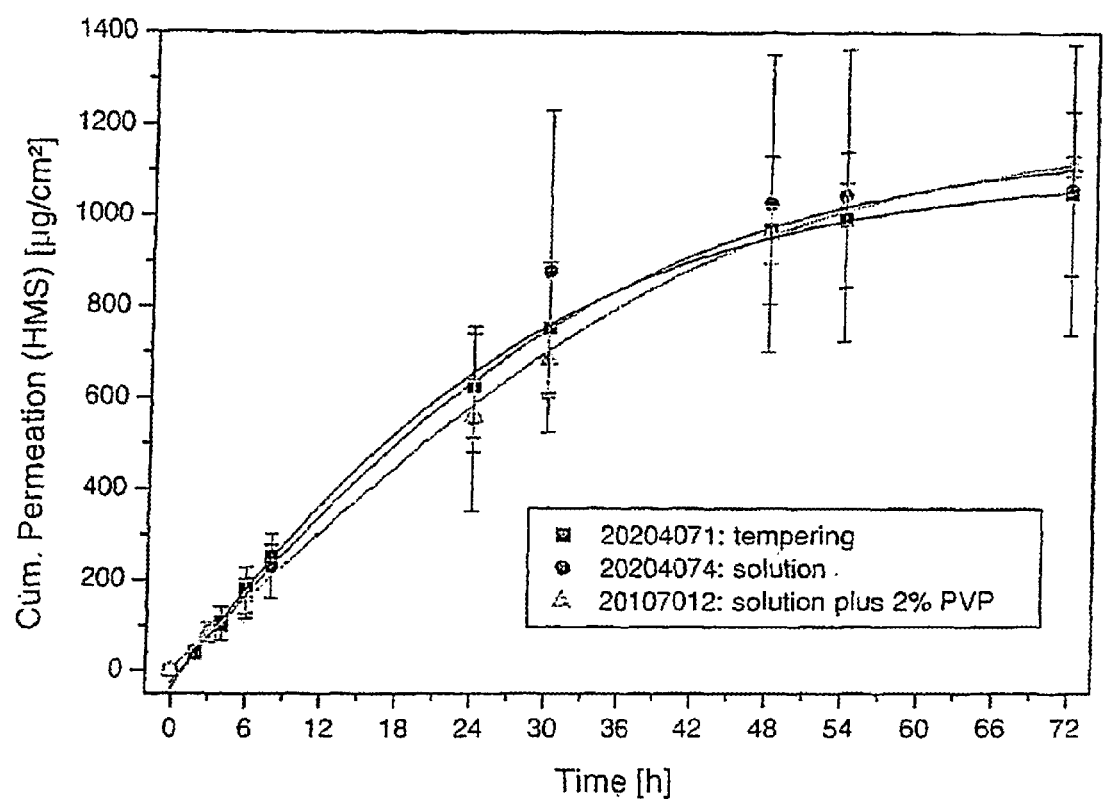
FIG. 3 shows the comparison of in vitro rotigotine flow rates that are achieved after applying on mouse skin a system according to the invention (Charge 20204071), a comparison charge (Charge 20204074) produced according to example of execution 2b in the solvent method without dispersants and a system described in WO 99/49852 (Charge 20107012).
Figure 4:
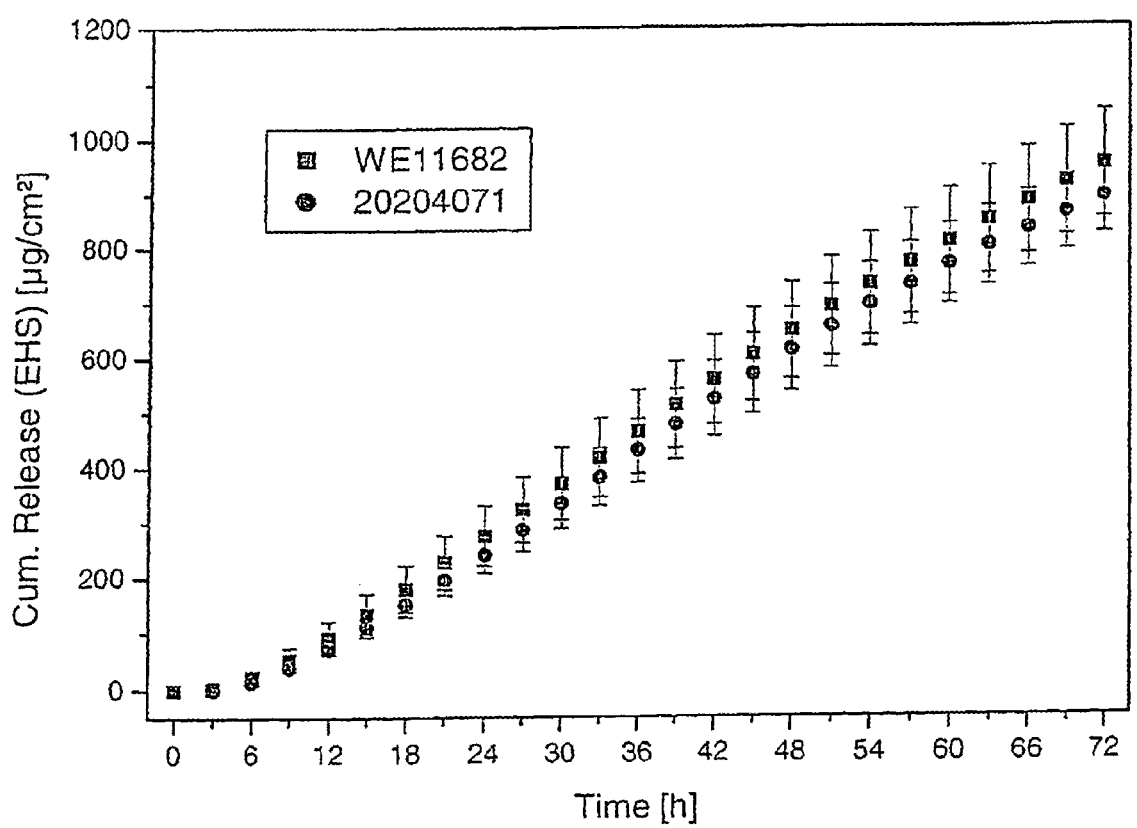
FIG. 4 shows the comparison of in vitro rotigotine flow rates that are achieved after applying on human skin a transdermal system according to the invention (Charge 20204071) after 5 months storage and a transdermal system described in WO 99/49852 (Charge WE11682).

Furthermore, it was shown in in vitro permeation experiments on mouse skin and human skin that when applied on the skin, transdermal systems that contain the silicon matrix-containing amorphous rotigotine particles produced according to the invention lead to rotigotine permeation rates that are nearly identical to the therapeutically usable TTSs produced in the solvent method according to WO 99/49852 (FIGS. 3 and 4). Even after five months storage at room temperature, the release behavior of the TTS according to the invention remained unchanged (FIG. 4).

This means that the adding of a solubilizer/dispergent to achieve a pharmacologically relevant flow rate of rotigotine from polymer matrixes is not necessary according to the invention.

Rather, therapeutically relevant flow rates can be achieved surprisingly with a very simply structured matrix, if the rotigotine not dissolved in the matrix polymer can be "conserved" finely distributed in amorphous particles in the matrix.

If this is successful, in that for example, by heating the matrix supersaturated with rotigotine the crystalline active substance form is converted into the amorphous form, which is then present in the matrix dispersed in fine distribution, it will not be necessary to add solubilizers, crystallization inhibitors and/or dispersants, e.g. in the form of polar innerphase polymers.

Since the supersaturated, preferably silicon-based matrixes do not contain any potentially peroxide-containing hydrophilic polymers such as PVP, the adding of additives to remove peroxide ("peroxide catchers") can also be dispensed with. Furthermore, the matrix also contains no anorganic silicates or skin penetration enhancers.

Even after 12 months storage, the TTS according to the invention show no signs of rotigotine recrystallization or any change in particle size. In addition, in vitro release experiments with the TTS according to the invention showed an unchanged release profile comparable with the collidone-containing TTS produced according to example 2a. Contrary to this, a crystalline, rotigotine-containing TTS produced according to example of execution 3, for which the step of heating above the melting point of rotigotine was dispensed with, provided a clearly lower active substance release.

Lastly, the use of softeners—typical in hot melting methods—to reduce the dynamic viscosity of matrix polymers can also be dispensed with, since the polymer is processed in the solvent method.

An object of the invention is thus a matrix for transdermal administering of rotigotine [(−)-5,6,7,8-tetrahydro-6-[propyl [2-(2-thienyl)ethyl]amino]-1-naphtol], containing a matrix polymer supersaturated with rotigotine base, characterized in that the portion of the rotigotine not dissolved in the matrix polymer is dispersed in the matrix polymer as amorphous particles with a maximum mean diameter of 30 μm and the matrix is free of solubilizers, crystallization inhibitors and dispersants.

A further object of the invention is a matrix containing rotigotine [(−)-5,6,7,8-tetrahydro-6-[propyl[2-(2-thienyl) ethyl]amino]-1-naphtol] and consisting of
(a) matrix polymer,
(b) rotigotine base in a concentration above the solubility limit of the matrix polymer, wherein the portion of the rotigotine not dissolved in the matrix polymer is dispersed in the matrix polymer as amorphous particles with a maximum mean diameter of 30 μm and
(c) optionally one or more antioxidants.

The matrix according to the invention generally contains at least 60 weight percent, preferably 70-95 weight percent, and particularly preferably 80-91 weight percent matrix polymer, each relative to the matrix weight.

In a preferred form of execution of the invention, the matrix polymer is a silicon, preferably an amino-resistant silicon or a silicon mixture.

A further object of the invention is thus a matrix containing rotigotine [(−)-5,6,7,8-tetrahydro-6-[propyl[2-(2-thienyl) ethyl]amino]-1-naphtol] and consisting of
(a) amino-resistant silicon,
(b) rotigotine base in a concentration above the solubility limit of the silicon, wherein the portion of the rotigotine not dissolved in the silicon is dispersed in the silicon as amorphous particles with a maximum mean diameter of 30 μm and
(c) optionally one or more antioxidants.

In this patent application the term "matrix" is understood to mean a pharmaceutical formula that comprises at least one matrix polymer and that can form a disperse system.

In this patent application the term "rotigotine base" is understood to mean that less than 5 weight percent, preferably less than 2 weight percent, and particularly preferably less than 1 weight percent of the rotigotine is present in salt form.

In this patent application the term "particles" is understood to mean microscopically visible rotigotine accumulations, e.g. in drop form, in the matrix.

The term "mean diameter" is understood to the mean the average value of all diameters (in the dimensions x, y, z, respectively) of the rotigotine particles present in a given matrix. This can be determined by examining the rotigotine-containing matrix with a microscope and analyzing the image with the Nikon LuciaDi software.

In this patent application the expression "matrix supersaturated with rotigotine" is understood to mean that at least a portion of the rotigotine is not in the form dissolved in the polymer but rather dispersed as particles in the matrix.

The term "matrix polymer" is understood to mean the polymers common for a pharmaceutical expert for producing transdermal forms of medicine. Examples of this are silicons, ethylvinyl acetates (EVA), styrol block copolymers (SXS), acrylates and methacrylates, polyurethanes, vinyl acetates and gums, in particular polyolefines and polyterpenes, e.g. polyisobutylenes, polybutadienes, neoprenes or polyisoprenes as well as suitable mixtures of these matrix polymers.

In this patent application the expression "silicon-based matrix" is understood to mean a matrix that contains at least 60 weight percent, preferably 70-95 weight percent, and particularly preferably 80-91 weight percent silicon, relative to the matrix weight.

In a preferred form of execution of the invention, matrix polymers are used in which rotigotine has a solubility of less than 5 weight percent, preferably less than 3 weight percent and particularly preferably less than 1 weight percent.

The matrix supersaturated with rotigotine can be used for processing in various galenic forms of medicine. In this connection, the rotigotine-containing matrix can be designed as an adhesive (self-adhesive) or non-adhesive matrix.

The amorphous rotigotine particles are present preferably dispersed in a self-adhesive matrix, particularly preferably in a self-adhesive silicon contact adhesive matrix.

Preferred silicon contact adhesives to use in the self-adhesive silicon contact adhesive matrix are amino-resistant, pressure-sensitive polyorganosiloxane adhesives.

Silicon contact adhesives are in most cases polydimethyl siloxanes, but in principle instead of methyl groups other organic residues, such as ethyl or phenyl groups, can also be present. Amino-resistant silicon contact adhesive are generally distinguished in that they contain no or only few free silanol functions, because the Si—OH groups were alkalized. Such adhesives are described in the patent EP 180 377.

Particularly preferable adhesives are condensates or mixtures of silicon resins and polyorganosiloxanes, as described in US RE 35 474, for example.

Suitable polyorganosiloxane adhesives are commercially available from Dow Corning as so-called BIO-PSA contact adhesives. Particularly suitable are contact adhesives that are marketed by Dow Corning under the designation Bio-PSA 7-4201 and Bio-PSA 7-4301, as well as suitable mixtures of these adhesives. These mixtures of silicon adhesives with strong and medium tack, in particular mixtures in Bio-PSA 7-4201 to Bio-PSA 7-4301 proportions of 40:60 to 60:40, are distinguished by a particularly favorable adhesion/cohesion balance.

The active substance concentration of the matrix according to the invention is not subject to the method-related limitations like the matrices produced in the solvent method according to the state of the art.

Since in the method according to the state of the art the crystalline rotigotine base is preliminarily dissolved in ethanol, the active substance charge is limited by the solubility of the rotigotine in the solvent used. A matrix charge with more than roughly 15 weight percent rotigotine is thus difficult in the known solvent method. This limitation is eliminated with the matrix produced according to the invention, because a preliminary dissolving of the rotigotine base in ethanol is not necessary.

For this reason, the incorporation of rotigotine base in concentrations above 15 weight percent is also possible. This is particularly helpful, for example, when a more lengthy rotigotine release from the matrix is desired, e.g. over 5, 6 or 7 days.

In principle, the active substance concentration in the matrix can be between 1 and roughly 40 weight percent relative to the total weight of the matrix, wherein rotigotine concentrations between 5 and 30 weight percent and particularly between 7 and 25 weight percent are preferred.

For a release of rotigotine from the matrix lasting 7 days, a rotigotine concentration in the matrix of at least 15 weight percent, and particularly of at least 20 weight percent, is preferred.

Antioxidants are added, preferably in a total concentration of up to 2 weight percent, preferably 0.05-0.5 weight percent (relative to the matrix weight). Preferred examples are alpha-tocopherol, ascorbyl palmitate and mixtures thereof.

In a preferred example of execution of the invention, the matrix according to the invention consists of
(a) 60-95 weight percent of a matrix polymer, preferably a silicon or silicon mixture,
(b) 1-40 weight percent, preferably 5-30 weight percent, and particularly preferably 7-20 weight percent amorphous rotigotine base dispersed in the matrix polymer, wherein the portion of the rotigotine not dissolved in the silicon is dispersed in the silicon as amorphous particles with a maximum mean diameter of 30 μm and
(c) 0-2 weight percent, preferably 0.05-0.5 weight percent antioxidant.

The size distribution of the rotigotine particles in the preferably silicon-based matrix supersaturated with rotigotine should be as uniform as possible, wherein the mean diameter should preferably be below 25 μm, and particularly preferably below 20 μm.

In a preferred form of execution, the matrix according to the invention is a component of a system, in particular a planiform system for transdermal administering of rotigotine, wherein the system can have further components such as, for example, a protective layer, a backing, further polymer layers and/or a membrane controlling the active substance delivery.

Figure 5:
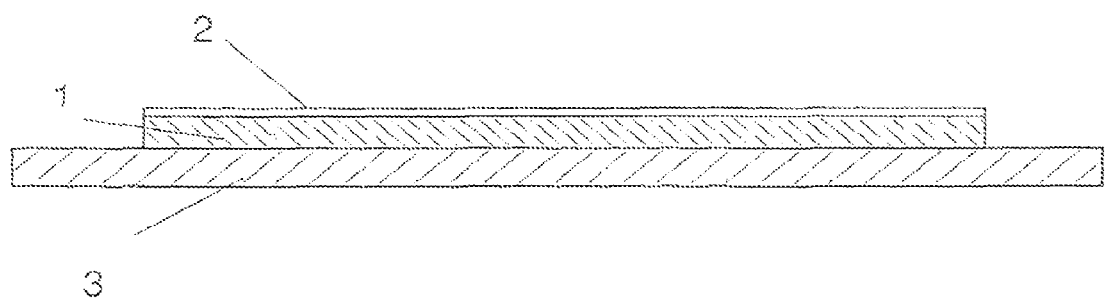
FIG. 5 shows as an example the structure of a monolithic TTS with an active substance-containing matrix (1), a backing (2) impermeable to the active substance and a protective layer (3) removable before utilization.
Figure 6:
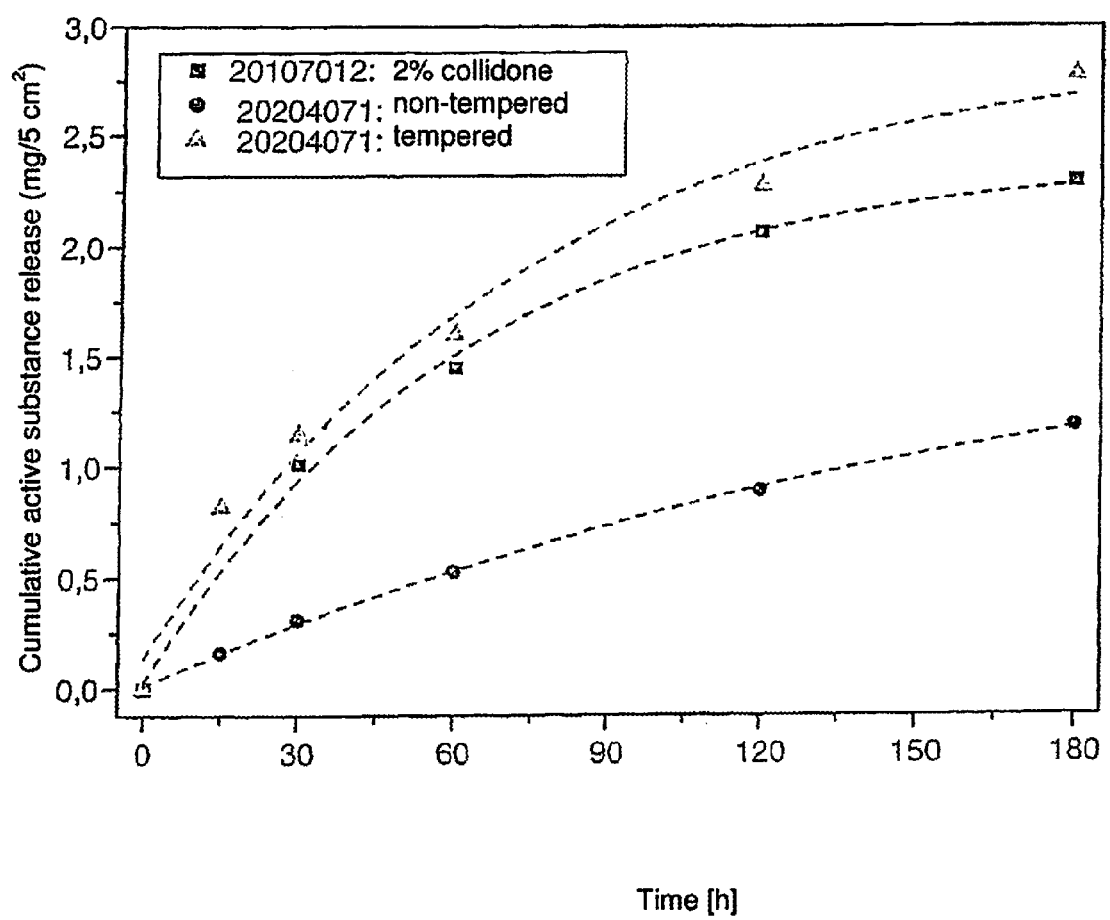
FIG. 6 shows a comparison of the in vitro penetration rates through mouse skin from the transdermal systems (Charge 20204071, tempered) according to the invention and from the comparative examples 2a (Charge 20107012) and 3 (Charge 20204071, non-tempered) after 12 months of storage.

In a particularly preferred form of execution of the invention, the system according to the invention is equipped as a so-called monolithic plaster, i.e., it consists of a backing (2) impermeable to the active substance, a self-adhesive, preferably silicon-based matrix (1) supersaturated with rotigotine and into which the free base of rotigotine is dispersed in amorphous form and which contains no solubilizer, and a layer (3) that can be removed before applying on the patient's skin, as illustrated in FIG. 5.

In other forms of execution of the invention, the rotigotine can also be present in a nonadhesive, supersaturated, preferably silicon-based matrix. The planiform system can then have an additional active substance-free adhesive layer or a so-called "overtape".

An object of the invention is thus a planiform system for transdermal administering of rotigotine [(−)-5,6,7,8-tetrahydro-6-[propyl[2-(2-thienyl)ethyl]amino]-1-naphtol], containing a rotigotine-containing matrix layer and a backing impermeable to the active substance, characterized in that the matrix layer consists of
(a) matrix polymer, preferably an amino-resistant silicon or a silicon mixture,
(b) rotigotine base in a concentration above the solubility limit of the matrix polymer, wherein the portion of the rotigotine not dissolved in the matrix polymer is dispersed in the matrix polymer as amorphous particles with a maximum mean diameter of 30 μm and
(c) optionally one or more antioxidants.

In a preferred form of execution of the invention, the planiform system is structured as a monolithic system and contains a self-adhesive rotigotine-containing matrix layer based on an amino-resistant silicon contact adhesive.

The surface of the system can be between 5 and approx. 80 cm² large, is preferably between 10 and 60 cm² and particularly preferably between 20 and 40 cm².

The thickness of the matrix layer in the systems according to the invention is typically in the 40-300 μm range, wherein matrix thicknesses of 50-200 μm and particularly of 70-150 μm are preferred. This results in a preferred matrix weight of approx. 40-200 g/m².

Preferred rotigotine concentrations in the matrix layer of the system are between 5 and 30 weight percent and particularly preferably between 7 and 25 weight percent, relative to the total weight of the matrix. If the system is intended for an application of more than 5 days, as a rule concentrations, of the rotigotine of more than 15 weight percent, and preferably more than 20 weight percent, are preferred. Typical concentrations for 7-day plasters are 20-30 weight percent.

In this connection, the charge level of the matrix in the system according to the invention is basically between 0.1 and 9 mg rotigotine/cm² matrix surface. The preferred charge level is in the 0.3-6 mg rotigotine/cm² range. For systems for daily or 2-day administering, a rotigotine charge between 0.3 and 1.5 mg rotigotine/cm² is preferred, and for 7-day systems one of 2.5-6.0 mg/cm².

The following table shows active substance concentrations and matrix weight of the monolithic plaster used for the skin permeation experiments (FIGS. 2, 3).

Rotigotine is a dopamine agonist. The matrices and systems according to the invention are thus particularly suitable for treating illnesses that are associated with a disturbed dopamine metabolism.

An object of the invention is thus the use of a system according to the invention or a matrix according to the invention in a drug for treating Morbus Parkinson, Restless Leg or depression.

The preferably silicon-based matrix supersaturated with rotigotine can be produced simply in that the rotigotine base in crystalline form is stirred into a solution of a corresponding matrix polymer, the solvent is removed by drying at 50° C. and finally, the solvent-free matrix is heated ("tempered") to a temperature above the melting point of rotigotine, i.e., above approx. 74° C. until the rotigotine crystals have melted. Subsequently, the matrix is cooled to room temperature, in such a way that the rotigotine is finally present in the form of amorphous particles or drops in the matrix according to the invention. The cooling step is preferably carried out "passively", i.e., the rotigotine-containing matrix is exposed to room temperature; an additional cooling is not necessary, as a rule.

An object of the invention is thus a method for producing a matrix for transdermal administering of rotigotine, characterized by the consecutive steps:

| Charge number | Production condition | Active substance concentration | Matrix weight (g/m²) | Cumulative flow through human skin μm/cm²/72 h | Cumulative flow through mouse skin μm/cm²/72 h |
|---|---|---|---|---|---|
| 20204071 | Tempered 90° C., 75 min. | 8.87 weight percent | 129 | 850 | 1030 |
| 20107012 | Solvent method [1] | 9 weight percent | 110 | n.d. | 1080 |
| WE 11682 | Solvent method [1] | 9 weight percent | 50 | 900 | n.d. |

[1] = comparison example corresponding to WO 99/49852; see example of execution 2a
n.d. = not determined The size distribution of the rotigotine particles in the silicon-based matrix of the systems according to the invention should be as uniform as possible and on the average below 30 μm, wherein the mean diameter is preferably below 25 μm, and particularly preferably below 20 μm.

In addition, in a given matrix layer there should preferably be no particles whose diameter in the largest dimension (x, y, z) is greater than 90% of the thickness of the respective matrix layer.

The backing onto which the matrix mass of the system according to the invention is spread should be inert for the contents of the matrix and impermeable to rotigotine. Suitable materials are, for example, polyesters, polyamides, polyethylenes, polypropylene, polyurethanes, PVC or combinations of these materials. The foils can be siliconized and/or provided with an aluminum layer. The thickness typically varies between 10 and 100 μm and is preferably between 20 and 40 μm.

The system also preferably contains a protective layer or foil that is removed immediately before using the system, i.e., before applying on the skin. This protective layer can, for example, be of polyester, polyethylene or polypropylene. This layer can additionally be coated with aluminum or fluoropolymers. The thickness of this protective layer is typically between 30 and 200 μm. For improved removal of the protective layer immediately before use, the protective layer preferably consists of two separate foils the ends of which may overlap. Corresponding designs are known from conventional plasters.

(a) dissolving the matrix polymer, e.g. the silicon, in a solvent, e.g. in heptane, ethyl acetate and toluol,
(b) adding rotigotine base in crystalline form in a quantity above the solubility limit of the polymer,
(c) removing the solvent and heating the matrix mass produced to a temperature of at least 74° C. until the rotigotine in the matrix mass has melted,
(d) cooling, preferably passively cooling the matrix mass.

In this connection, in step (c) the removal of the solvent and the melting of the rotigotine can be achieved by continually raising the temperature, e.g. from 50° C. to 90° C., in a dry lane.

As an alternative, in step (c) the solvent can first be removed in a step (c1) at a temperature of 40-60° C. and the solvent-free matrix can then be heated in a step (c2) to at least 74° C. until the rotigotine has melted.

Suitable process temperatures for the melting of rotigotine are, for example, 75-120° C., preferably 80-100° C., and particularly preferably 90° C.

If a system according to the invention is to be produced that has, in addition to the rotigotine-containing matrix, a backing that is impermeable to the active substance, the rotigotine-containing polymer mass created during the above-described matrix production in step (b) is spread out on a suitable foil, e.g. a polyester foil, before removal of the solvent.

An object of the invention is thus a method for producing a planiform system for transdermal administering of rotigotine, comprising a rotigotine-containing matrix, characterized by the consecutive steps:

(a) dissolving the matrix polymer, e.g. the silicon, in a solvent,
(b) adding rotigotine base in crystalline form in a quantity above the solubility limit of the polymer,
(c) spreading out the rotigotine-containing polymer mass on a suitable foil,
(d) removing the solvent and heating the matrix mass produced to a temperature of at least 74° C. until the rotigotine in the matrix mass has melted,
(e) cooling, preferably passively cooling the matrix mass.

In this connection, removal of the solvent and the melting of the rotigotine according to step (d) can take place either by continually raising the temperature, e.g. from 50° C. to 90° C. or, on the other hand, in stages in two separate steps (d1) and (d2), as already described further above.

Before adding the crystalline rotigotine, the usually needle-shaped rotigotine crystals can be reduced to the desired size, e.g. 50 µm long, if necessary, by suitable pre-treatment, e.g. by grinding or pounding and subsequent sifting.

Experimental Section:
1. Production of a Silicon-Based System According to the Invention 1.8 g crystalline rotigotine (free base) was ground and added as powder with a grain size below 40 µm to a 74% (g/g) solution of silicon polymers in heptane (corresponds to 9 g Bio-PSA 7-4201 and 9 g Bio-PSA 7-4301). The mixture was stirred with an Ultraturrax at 10,000 rpm for 1 minute to produce a homogenous dispersion. Subsequently the rotigotine-containing silicon mass was spread out on a Scotch Pak 1109 foil (6 mm/sec) and dried for 30 minutes at 50° C. Finally, protective foil (MN 19) was applied.

It was then dried for 75 minutes at 90° C.

2. Comparison Examples: Production of the Silicon-Based Matrix in the Solvent Method According to the State of the Art with (Example 2a) or without (Example 2b) Adding PVP 1.8 g crystalline rotigotine (free base) was ground and, dissolved in 4 g ethanol (96%) with or without 2.4 g collidone (PVP), was added into a 74% (g/g) solution of silicon polymers in heptane (corresponds to a mixture of 9 g Bio-PSA 7-4201 and 9 g Bio-PSA 7-4301). The mixture was stirred with an Ultraturrax at 10,000 rpm for 1 minute to produce a homogenous dispersion. Subsequently the rotigotine-containing silicon mass was spread out on a Scotch Pak 1109 foil (6 mm/sec) and dried for 30 minutes at 50° C. Finally, protective foil (MN 19) was applied.

3. Production of a Silicon-Based Matrix without Preliminary Dissolving and Tempering 1.8 g crystalline rotigotine (free base) was ground and added as powder with a grain size below 40 µm to a 74% (g/g) solution of silicon polymers in heptane (corresponds to 9 g Bio-PSA 7-4201 and 9 g Bio-PSA 7-4301). The mixture was stirred with an Ultraturrax at 10,000 rpm for 1 minute to produce a homogenous dispersion. Subsequently the rotigotine-containing silicon mass was spread out on a Scotch Pak 1109 foil (6 mm/sec) and dried for 30 minutes at 50° C. Finally, protective foil (MN 19) was applied.

4. Example: Determining the Active Substance Flow in the Mouse Skin Model

For the flow measurements through mouse skin, stomach, and back skin with a thickness of approx. 120 to 150 µm was used. A TTS with a punched out surface of 2.55 cm² is fixed in a horizontal diffusion cell on the corneum side of the skin of the stomach and back of hairless mice. Immediately afterward, the acceptor chamber of the cell is filled free of air bubbles with phosphate powder solution (0.066 molar) pre-tempered at 32° C., pH 6,2 and the release medium is regulated by thermostat at 32±0.5° C. At the sample removal times, the release medium is exchanged for fresh medium regulated by thermostat at 32±0.5° C. The rotigotine release is determined by HPLC.

5. Example: Determining the Active Substance Flow in the Human Skin Model

The determination of the rotigotine flow through human skin was essentially carried out as described in H. Tanojo et al., J. Control Rel. 45 (1997) 41-47.

For this, human skin with a thickness of 250 µm was obtained from the abdomen. A TTS with a surface of 2.545 cm² was applied on this same surface area of human skin, wherein the skin rests on a silicon membrane toward the acceptor side. The acceptor phase used was PBS (0.066 molar), pH 6,2 and a temperature of 32±0.5° C. The experiments were conducted for 72 hours with a flow of 5 mL/h. At the sample removal times, the release medium is exchanged for fresh medium regulated by thermostat at 32±0.5° C. and the quantity of the rotigotine released is measured by HPLC. The flow rate Q(t) was determined relative to the surface of the measuring cell (0.552 cm²).

The invention claimed is:

1. A matrix for transdermal administration of rotigotine that is storage-stable for at least 6 months, the matrix comprising
(a) a matrix polymer, and
(b) rotigotine base in a concentration above the solubility limit of rotigotine base in the matrix polymer,
wherein a portion of the rotigotine base not dissolved in the matrix polymer is dispersed in the matrix polymer as amorphous particles with a maximum mean diameter of 30 µm, and wherein the matrix is free of solubilizer, crystallization inhibitor and dispersant.

2. A matrix for transdermal administration of rotigotine that is storage-stable for at least 6 months, the matrix consisting of:
(a) matrix polymer that is an amine-resistant silicone or a mixture of amine-resistant silicones,
(b) rotigotine base in a concentration above the solubility limit of rotigotine base in the matrix polymer, wherein a portion of the rotigotine base not dissolved in the matrix polymer is dispersed in the matrix polymer as amorphous particles with a maximum mean diameter of 30 µm, and
(c) optionally one or more antioxidants.

3. The matrix of claim 1, wherein the matrix polymer is an amine-resistant silicone or a mixture of amine-resistant silicones.

4. The matrix of claim 1 or 2 wherein the matrix is self-adhesive.

5. The matrix of claim 1 or 2 wherein the matrix consists of:
(a) about 60 to about 95 weight percent of an amine-resistant silicone or an amine-resistant silicone mixture,
(b) about 5 to about 40 weight percent amorphous rotigotine base dispersed in the silicone, and
(c) zero to about 2 weight percent antioxidant.

6. A system for transdermal administration of rotigotine comprising a matrix of claim 1 or 2 and a backing.

7. The system of claim 6 wherein the backing is impermeable to rotigotine.

8. The system of claim 6 wherein the rotigotine is present in an amount of 0.3 to 6 mg/cm².

9. The system of claim 6, wherein the rotigotine base is present in an amount permitting a flow rate of rotigotine through human skin that is therapeutically effective, upon application of the system at intervals of 1 to 7 days, for treatment of Morbus Parkinson.

10. The system of claim 6, wherein the rotigotine base is present in an amount permitting a flow rate of rotigotine through human skin that is therapeutically effective, upon application of the system at intervals of 1 to 7 days, for treatment of restless leg syndrome.

11. The system of claim 6, wherein the rotigotine base is present in an amount permitting a flow rate of rotigotine through human skin that is therapeutically effective, upon application of the system at intervals of 1 to 7 days, for treatment of depression.

* * * * *

UNITED STATES PATENT AND TRADEMARK OFFICE
CERTIFICATE OF CORRECTION

PATENT NO. : 8,545,872 B2
APPLICATION NO. : 13/020414
DATED : October 1, 2013
INVENTOR(S) : Armin Breitenbach Page 1 of 1

It is certified that error appears in the above-identified patent and that said Letters Patent is hereby corrected as shown below:

In the Specification

Column 2, line 39, replace "a system" with -- a transdermal system --.

Column 3, line 9, replace "dispergent" with -- dispersant --.

Column 3, line 43, replace "solubilizer/dispergent" with -- solubilizer/dispersant --.

Signed and Sealed this
Tenth Day of December, 2013

Margaret A. Focarino
*Commissioner for Patents of the United States Patent and Trademark Office*